United States Patent [19]
Brown

[11] Patent Number: 5,423,836
[45] Date of Patent: Jun. 13, 1995

[54] ENDOSCOPIC KNOT TYING TOOL AND METHOD

[75] Inventor: Scott C. Brown, Princeton, N.J.

[73] Assignee: PA Consulting Group, Hightstown, N.J.

[21] Appl. No.: 124,675

[22] Filed: Sep. 22, 1993

[51] Int. Cl.[6] .............................. A61B 17/00
[52] U.S. Cl. ................... 606/148; 606/139; 606/144
[58] Field of Search ........... 606/139, 211, 144–148; 112/169, 80.03

[56] References Cited

U.S. PATENT DOCUMENTS

| | | | |
|---|---|---|---|
| 957,154 | 5/1910 | Gallinek | 112/80.03 |
| 960,738 | 6/1910 | Turk | 112/80.03 |
| 3,476,114 | 11/1969 | Shannon et al. | |
| 3,665,926 | 5/1972 | Flores | |
| 4,204,541 | 5/1980 | Kapitanov | 606/145 |
| 4,417,532 | 11/1983 | Yasukata | 112/169 |
| 4,597,390 | 7/1986 | Mulhollan et al. | |
| 4,683,885 | 8/1987 | Hutterer et al. | |
| 4,760,848 | 8/1988 | Hasson | |
| 5,037,433 | 8/1991 | Wilk et al. | 606/139 |
| 5,059,201 | 10/1991 | Asnis | 606/144 |
| 5,078,721 | 1/1992 | McKeating | 606/139 |
| 5,129,912 | 7/1992 | Noda et al. | 606/139 |
| 5,152,769 | 10/1992 | Baber | 606/145 |
| 5,181,919 | 1/1993 | Bergman et al. | 606/144 |
| 5,192,287 | 3/1993 | Fournier et al. | 606/139 |
| 5,201,744 | 4/1993 | Jones et al. | 606/148 |
| 5,269,791 | 12/1993 | Mayzels et al. | 606/139 |
| 5,281,236 | 1/1994 | Bagnato et al. | 606/139 |
| 5,284,485 | 2/1994 | Kammerer et al. | 606/148 |

FOREIGN PATENT DOCUMENTS 4114204 11/1992 Germany .............. 606/148

OTHER PUBLICATIONS

*Suturer-Marbel*, Jun. 26, 1926 (one page).

*Primary Examiner*—Stephen C. Pellegrino
*Assistant Examiner*—Jeffrey A. Schmidt
*Attorney, Agent, or Firm*—Panitch Schwarze Jacobs & Nadel

[57] ABSTRACT

A method and a tool for tying a stitch knot. The tool comprises a first elongated member and a grasping member. The first elongated member includes a helix on one end. The helix has a filament extending from the first end, and a threading device is attached to the free end of the filament. The grasping member is separate and apart from the first elongated member, and includes an elongated shaft. A grasper is mounted on the first end of the shaft, and a portion of the shaft near the grasper is sized to reside within the helix for axial movement therewith. The method for tying the stitch knot involves positioning the shaft within the helix. The grasper is used to insert the threading device and pull the free end of the filament through an area to be stitched, and then to grasp the free end of the filament near the threading device. The grasping member is removed from the inner space of the helix, thus drawing the free end of the filament through the helix. When the grasping member and helix are moved apart from each other and the filament is removed from the helix, a loop for the stitch knot is formed. Moving the grasping member and helix further apart tightens the loop to the area to be stitched.

13 Claims, 2 Drawing Sheets

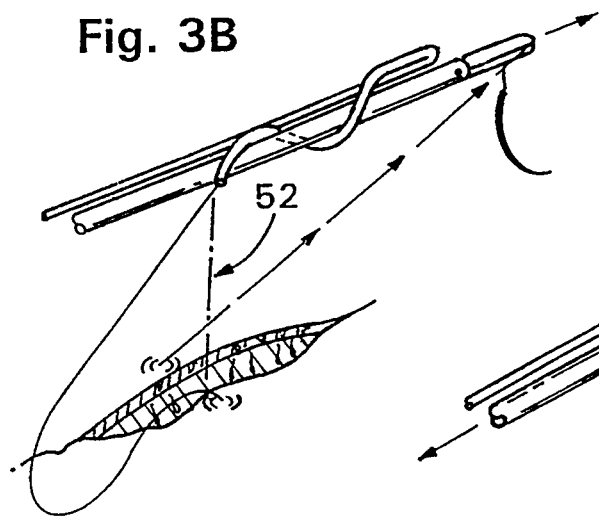
Fig. 3B
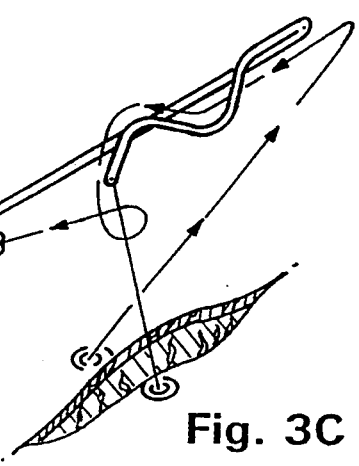
Fig. 3C
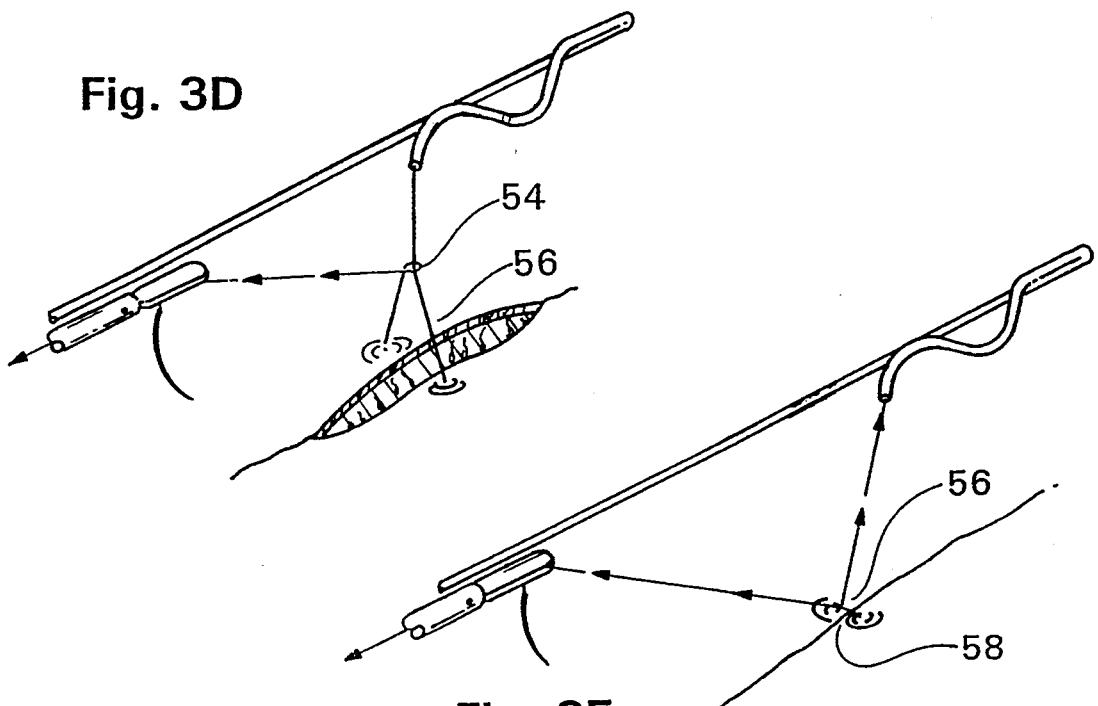
Fig. 3D
Fig. 3E

ENDOSCOPIC KNOT TYING TOOL AND METHOD

FIELD OF THE INVENTION

The present invention relates to a tool for tying a knot in a thread, a filament or the like. More particularly, the present invention relates to a method and apparatus for endoscopically tying a knot in a suture or sewing thread, where the thread has been passed through a wound disposed within a bodily cavity.

BACKGROUND OF THE INVENTION

Different techniques and tools are known for endoscopically stitching wounds disposed in a bodily cavity. Typically, a suture thread is inserted through the wound and tied through the use of multiple tools operating in a plurality of axes. However, and due to the physical confinements incumbent in endoscopic surgery, the already-known techniques and tools require considerable effort, patience, and time in order that the necessary manipulations be performed.

The present invention alleviates the aforementioned problems inherent in previous endoscopic suture tying techniques and tools by providing a single tool that both inserts the suture thread through the wound and causes a knot to be tied in the suture thread. Additionally, the tool provided by the present invention requires manipulation only in a singular longitudinal axis in order that a loop be created in the suture thread and tightened down to the wound. Thus, a knot may more easily be endoscopically tied in a suture thread at a wound disposed within a bodily cavity.

SUMMARY OF THE INVENTION

Briefly stated, the present invention comprises a method and a tool for tying a stitch knot. The knot tying tool comprises a first elongated member and a grasping member.

The first elongated member includes a helix on one end thereof, the helix having first and second ends, a helical axis, and an inner space. The helix also has a filament extending from the first end, the filament having a free end with a threading device attached thereto. The grasping member is separate and apart from the first elongated member, and includes an elongated shaft with first and second ends. A grasper is mounted on the first end of the shaft, and a portion of the shaft near the grasper is sized to reside within the inner space of the helix for axial movement with respect to the helix.

The method for tying the stitch knot involves positioning the shaft within the inner space of the helix by axially inserting the grasper through the helix. After using the grasper to insert the threading device and pull the free end of the filament through an area to be stitched, the free end of the filament is grasped near the threading device. Thereafter, the grasping member is removed from the inner space of the helix, thus drawing the free end of the filament through the helix. When the grasping member and helix are moved apart from each other and the filament is removed from the helix, a loop for the stitch knot is formed. Moving the grasping member and helix further apart tightens the loop to the area to be stitched.

BRIEF DESCRIPTION OF THE DRAWINGS

The foregoing summary, as well as the following detailed description of the preferred embodiment of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIGS. 3A–3E show perspective views of the tool in stages as suture thread is sewn through a wound and as a knot is created in the suture thread.

DETAILED DESCRIPTION OF PREFERRED EMBODIMENTS

Figure 1:
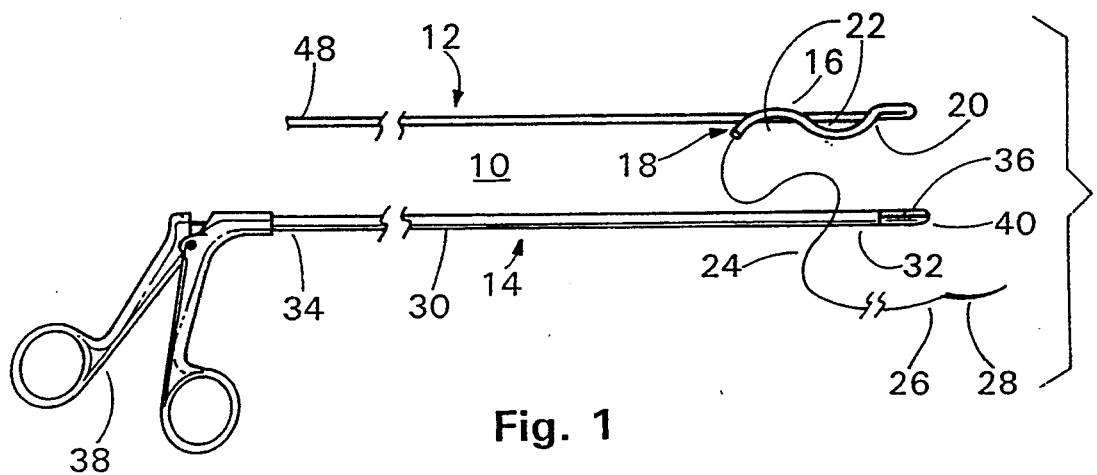
FIG. 1 is an exploded perspective view showing both ends of both members of the preferred embodiment of the present invention.

Certain terminology may be used in the following description for convenience only and is not limiting. The words "right", "left", "upper" and "lower" designate directions in the drawings to which reference is made. The words "inwardly" and "outwardly" refer to directions toward and away from, respectively, the geometric center of the referenced element. The terminology includes the words above specifically mentioned, derivatives thereof, and words of similar import.

Referring to the drawings in detail, wherein like numerals are used to indicate like elements throughout, there is shown in FIG. 1 a knot tying tool or apparatus 10 comprising a first elongated member 12 and a grasping member 14. As can be seen from FIGS. 3A–3E, the first elongated member 12 and the grasping member 14 are constructed to combine into a single unit.

The first elongated member 12 includes a helix 16 on one end. The helix 16 has first and second ends 18, 20 and an inner or core space 22 through which a helical axis extends. A filament or suture sewing thread 24 extends from the first end 18 of the helix 16. The thread 24 can be attached to the first end 18 by any of a number of well-known methods. As can be seen, the filament 24 has a free end 26 with a suturing needle or a threading device 28 attached thereto.

As also seen in FIG. 1, the first elongated member 12 has a manipulating staff 48 attached to the helix 16 at the second end 20 of the helix 16. The manipulating staff 48 extends from the helix 16 to permit a user to remotely manipulate the helix 16.

The grasping member 14 is separate and apart from the first elongated member 12, and may be combined with and detached from the first elongated member 12, as will be described below. The grasping member 14 includes an elongated shaft 30 having first and second ends 32, 34. A grabbing device or grasper 36 is mounted on the first end 32 of the elongated shaft 30, and a grasper controller 38 for controlling the grasper 36 is mounted on the second end 34. Control lines or the like (not shown) extend through the shaft 30 between the grasper controller 38 and the grasper 36. The grasper 36 may have one or more jaws 40 adapted to grab and securely hold bodily tissue, surgical implements, and the like, including the threading device 28 and the filament 24. Both the grasper 36 and the grasper controller 38 are well known in the art and, therefore, will not be described further.

In order that the first elongated member 12 and grasping member 14 may be combined and separated at will, at least a portion of the shaft 30 of the grasping member 14 located proximate to the grasper 36 is sized to reside within the inner space 22 of the helix 16. The grasper 40 is similarly sized such that the shaft 30 may be inserted through the helix 16, shaft first end 32 being inserted into the helix 16 at helix first end 18. Thus, the shaft 30 is adapted to axially move with respect to the helix 16, the grasper 36 protruding from the second end 20 of the helix 16 and at least a portion of the shaft 30 residing within the inner space 22 of the helix 16.

With the grasping member 14 and the first elongated member 12 combined, and with the grasper 36 protruding from the second end 20 of the helix 16, the tool 10 may be maneuvered to grasp the threading device 28 and pass the threading device 28 through an area to be stitched. A loop is created in the filament 24 by grasping the free end of the filament 24, moving the grasping member 14 axially with respect to the helix 16, passing the free end of the filament 24 through the helix 16, and removing the filament 24 from the helix 16.

Figure 2:
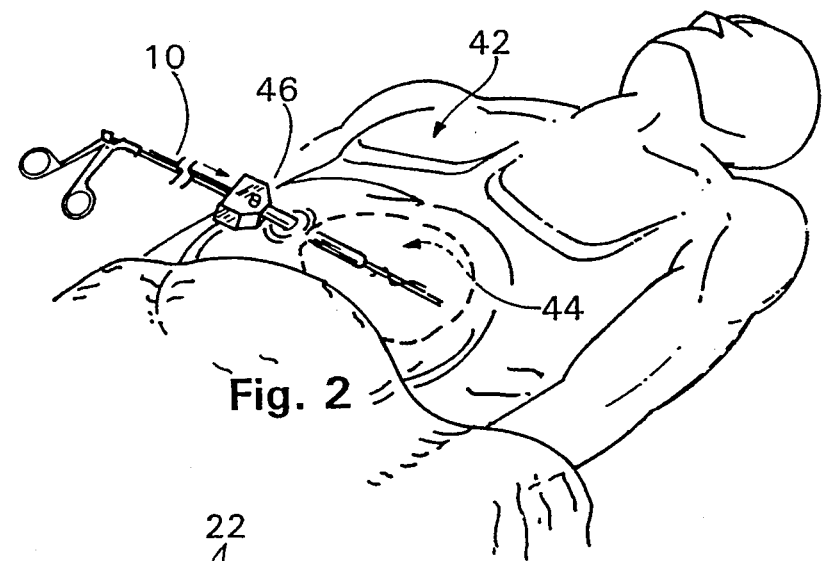
FIG. 2 is a plan view of the tool of FIG. 1 endoscopically inserted into a bodily cavity.

As can be seen in FIG. 2, the tool 10 may be inserted within a body 42 and into a bodily cavity 44 by way of an endoscope 46. With the tool 10 introduced into the endoscope 46, the manipulating staff 48 may be used to externally and remotely manipulate the helix 16 while the helix 16 is disposed within the bodily cavity 44. Similarly, the grasping member 14 may be externally and remotely manipulated at the second end 34, and the grasper 30 may be controlled by way of the grasper controller 38. Thus, a wound 48 within the bodily cavity 44 may be sutured according to the method described below.

As shown in the drawings, the helix 16 has one full turn. That is to say, the helix 16 turns around the helical axis about 360 degrees. As should be evident, the helix 16 may comprise a predetermined number of full turns. However, the number of full turns must be at least one for the tool 10 to function correctly.

Both the grasping member 14 and the first elongated member 12 are constructed from high-strength, lightweight materials. The materials must be able to be formed into extremely narrow, lengthy pieces, and yet maintain their relative shapes under the stress and strain of an endoscopic procedure. The material employed in the first elongated member 12 must be able to be formed into a helix 16 of a size that can be inserted through the endoscope 46, and the material employed in the grasping member 14 must similarly be able to be formed into a hollow shaft 30. Such materials may include surgical stainless steel and a variety of polymers, although many other materials having the required characteristics are known and may also be utilized.

Figure 3A:
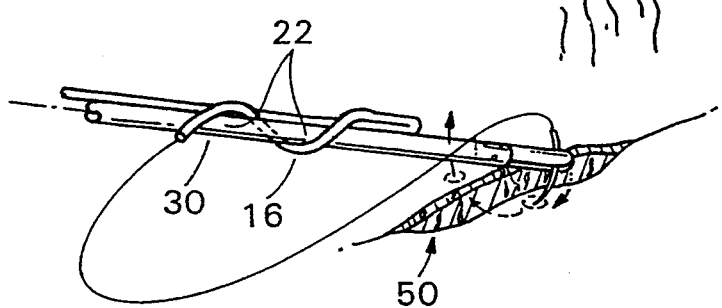

A method for tying a stitch knot using the knot tying tool 10 will now be described. Preliminarily, and as shown in FIG. 3A, the shaft 30 must be positioned within the inner space 22 of the helix 16. The shaft 30 is thus positioned by axially inserting the grasper 36 through the inner space 22 of the helix 16 at the first end 18 thereof such that the grasper 36 protrudes from the second end 20 of the helix 16, with a portion of the shaft 30 adjacent to the grasper 36 residing within the inner space 22 of the helix 16.

The helix 16 having already been arranged to have a filament 24 extending from the first end 18 thereof, and with the shaft 30 thus positioned, the tool 10 is maneuvered to grasp the threading device 28 with the grasper 36 and insert the threading device 28 through a wound 50. Such insertion typically would include the steps of inserting the threading device 28 down and into tissue on one side of the wound 50, and then passing the threading device 28 up, through, and out of tissue on the other side of the wound 50. However, numerous other suture insertion techniques are contemplated. With the threading device 28 thus inserted, the grasper 36 may then be manipulated to grasp the now-protruding tip of the threading device 28 and to pull the free end 26 of the filament 24 through the wound 50.

As shown in FIG. 3B, the tool 10 may then be manipulated to grasp the free end 26 of the filament 24 proximate the threading device 28. Thereafter, the tool 10 is moved in a generally longitudinal manner such that the first end 18 of the helix 16 is approximately directly over the area in the wound 50 where the filament 24 has been passed through. In such a position, an imaginary line 52 extends from the first end 18 of the helix 16 to the area where the filament 24 passes through the wound 50 at approximately a right angle with respect to the wound 50.

With the tool 10 thus positioned, and now referring to FIG. 3C, the grasping member 14 is removed from the inner space 22 of the helix 16 by passing the grasper 36 axially through the inner space 22 in the direction opposite to the direction of insertion. When the grasper 36 is withdrawn from the helix 16 at the first end 18 thereof, the free end 26 of the filament 24 and the threading device 28 are axially passed through the inner space 22 and extend out from the inner space 22 at the first end 18 of the helix 16.

As can be seen in FIG. 3D, when the grasping member 14 and the helix 16 are moved apart from each other, the filament 24 slips off the helix and a loop 54 is formed. As shown in FIG. 3E, the loop 54 is tightened to the wound 50 to make a stitch knot 56 by moving the grasping member 14 and the helix 16 even further apart. Thus, a suture 58 is created and secured in the wound 50 disposed within the bodily cavity 44 by a knot tying tool 10 endoscopically inserted within the bodily cavity 44.

As previously mentioned, the helix 16 comprises a predetermined number of full turns, with the number of full turns being at least one full turn. As may be recognized, the filament 24 passes through the loop 54 a number of passes corresponding to the number of full turns of the helix 16. For example, the filament 24 shown in FIG. 3D passes through the loop 54 once since the helix 16 has one full turn.

In order that the stitch knot 56 may be secured to the wound 50, a second loop (not shown) may be created in a manner similar to the first loop 54. Thus, after releasing the free end 26 of the filament 24 from the grasper 36, the shaft 30 of the grasping member 14 is repositioned within the inner space 22 of the helix 16 in a manner consistent with that shown in FIG. 3A. The second loop may then be created by repeating the method steps shown in FIGS. 3B–3E and described above. Of course, the second loop does not require that the insertion device 28 and the free end 26 of the filament 34 be passed through the wound 50. When the second loop is tightened to the stitch knot 56, the stitch knot 56 is especially secure. As should now be evident, additional loops 54 may be created and tightened to the stitch knot 56 in order to secure the stitch knot 56 still further.

With the stitch knot 56 thus tied, the portions of the filament 24 extending from the suture 58 may be severed, and the first elongated member 12 and the grasping member 14 may be endoscopically removed from the bodily cavity 44 and the body 42. Alternatively, other sutures 58 may be placed in the wound 50 or in another wound 50. To that end, multiple filaments 24 may be attached to the helix 16 at the first end thereof, each filament having a fastening device 28.

From the foregoing description, it can be seen that the present invention comprises a new and useful method and apparatus for endoscopically tying a stitch knot or suture. It will be appreciated by those skilled in the art that changes could be made to the embodiments described above without departing from the broad inventive concepts thereof. It is understood, therefore, that this invention is not limited to the particular embodiments disclosed, but it is intended to cover modifications within the spirit and scope of the present invention as defined by the appended claims.

I claim:

1. A method for tying a stitch knot in a wound disposed within a bodily cavity using a knot tying apparatus comprising a first elongated member and a grasping member, the first elongated member including a helix having a predetermined fixed shape including first and second ends, a helical axis, and an inner space, the helix having a filament extending from the first end, the filament having a free end with a threading device attached thereto, the grasping member being separate and apart from the first elongated member and including an elongated shaft with first and second ends and a grasper mounted on the first end of the shaft, a portion of the shaft adjacent the grasper being sized to reside within the inner space of the helix for axial movement with respect to the helix, the method comprising manipulating the grasping member in the helical axis while performing the steps of:

inserting endoscopically the first elongated member and the grasping member within the bodily cavity through a single external incision;

positioning the shaft within the inner space of the helix, the grasper being axially inserted through the helix at the first end such that the grasper protrudes from the second end of the helix and the portion of the shaft adjacent the grasper resides within the inner space of the helix;

inserting the threading device and pulling the free end of the filament through the wound, the grasper grasping the threading device during the inserting and pulling;

grasping the free end of the filament proximate the threading device with the grasper;

removing the grasping member from the inner space of the helix, the grasper being axially passed through the inner space and withdrawn from the helix at the first end thereof, the free end of the filament and the threading device being axially passed through the inner space and extending out from the inner space at the first end of the helix;

moving the grasping member and helix apart from each other, removing the filament from the helix, and forming a loop for the stitch knot; and tightening the loop to the wound.

2. The method of claim 1 wherein the first elongated member includes a manipulating staff attached to the second end of the helix, the manipulating staff extending remotely from the helix, the method further comprising the step of manipulating the helix remotely.

3. The method of claim 1 wherein the grasping member further includes a grasper controller, the controller disposed proximate the second end of the elongated shaft, the method further comprising the step of controlling the grasper from the second end of the elongated shaft.

4. The method of claim 1 wherein the fixed shape of the helix further comprises a predetermined number of full turns, the number of full turns being at least one full turn, the method further comprising the step of forming a number of filament passes through the loop, the number of passes corresponding to the number of full turns of the helix.

5. The method of claim 1 further comprising the step of moving the apparatus longitudinally such that the first end of the helix is approximately directly over the wound, and such that an imaginary line extends from the first end of the helix to the wound at approximately a right angle with respect to the wound.

6. The method of claim 1 further comprising the steps of:

releasing the free end from the grasper;

repositioning the shaft of the grasping member within the inner space of the helix;

forming a second loop by repeating the grasping, removing, and moving steps; and tightening the second loop.

7. A knot tying apparatus comprising:

a first elongated member having a longitudinal axis and including a helix having a predetermined fixed shape including first and second ends, a helical axis substantially in alignment with the longitudinal axis of the first elongated member, and an inner space, the, and an inner helix for receiving a filament having a free end with a threading device attached thereto; and a grasping member separate and apart from the first elongated member and including an elongated shaft with first and second ends and a grasper mounted on the first end of the shaft, a portion of the shaft being sized to reside within the inner space of the helix for axial movement with respect to the helix, wherein the threading device may be grasped by the grasper and passed through an area to be stitched, and wherein a loop is created in the filament when the free end of the filament is grasped by the grasper and the grasping member is moved axially with respect to the helix such that the free end of the filament passes through the helix and the filament is removed from the helix.

8. The apparatus of claim 7 further comprising an endoscopic insertion device, the first elongated member and the grasping member for being endoscopically inserted within a bodily cavity through the device to suture a wound disposed within the bodily cavity.

9. The apparatus of claim 7 wherein the first elongated member includes a manipulating staff attached to the second end of the helix, the manipulating staff extending from the helix for manipulating the helix remotely.

10. The apparatus of claim 7 wherein the grasping member further includes a grasper controller, the controller disposed proximate the second end of the elongated shaft.

11. The apparatus of claim 7 wherein the fixed shape of the helix comprises a predetermined number of full turns, the number of full turns being at least one full turn.

12. The apparatus of claim 11 further in combination with the filament, wherein the filament passes through the created loop a number of passes, the number of passes corresponding to the number of full turns of the helix.

13. The apparatus of claim 7 in combination with the filament and the threading device, wherein the filament is a suture sewing thread and wherein the threading device is a suturing needle.

* * * * *